(12) United States Patent
Su

(10) Patent No.: US 7,823,323 B2
(45) Date of Patent: Nov. 2, 2010

(54) REMOTE MONITORING SYSTEM FOR DETECTING TERMITES

(75) Inventor: Nan Yao Su, Davie, FL (US)

(73) Assignee: University of Florida Research Foundation Inc., Gainesville, FL (US)

( * ) Notice: Subject to any disclaimer, the term of this patent is extended or adjusted under 35 U.S.C. 154(b) by 1493 days.

(21) Appl. No.: 10/161,519

(22) Filed: Jun. 3, 2002

(65) Prior Publication Data

US 2002/0144453 A1    Oct. 10, 2002

Related U.S. Application Data

(63) Continuation of application No. 08/467,552, filed on Jun. 6, 1995, now Pat. No. 6,397,516, which is a continuation of application No. 08/323,582, filed on Oct. 17, 1994, now abandoned, which is a continuation of application No. 08/062,868, filed on May 17, 1993, now abandoned, which is a continuation-in-part of application No. 07/975,317, filed on Nov. 12, 1992, now abandoned, which is a continuation-in-part of application No. 07/891,896, filed on Jun. 1, 1992, now abandoned.

(51) Int. Cl.
*A01M 1/20* (2006.01)

(52) U.S. Cl. .................................. 43/131; 43/132.1
(58) Field of Classification Search ............... 43/134, 43/131, 132.1
See application file for complete search history.

(56) References Cited

U.S. PATENT DOCUMENTS

4,485,582 A    12/1984   Morris

FOREIGN PATENT DOCUMENTS

| JP | 60-64076 | * | 5/1985 |
| JP | 2-42003 | * | 3/1990 |
| JP | 63-56240 | * | 4/1992 |

* cited by examiner

*Primary Examiner*—Christopher P Ellis
(74) *Attorney, Agent, or Firm*—McDonnell Boehnen Hulbert & Berghoff

(57) ABSTRACT

The subject invention pertains to materials and methods useful for management of certain pests. The invention is particularly well suited for the control of social insect pests and, particularly, termites. The invention concerns unique toxicant-containing matrices as well as apparatuses for monitoring pest activity and presenting a toxicant. The invention is useful as part of an Integrated Pest Management Program and can greatly reduce the introduction of harmful chemicals into the environment.

17 Claims, 8 Drawing Sheets

Figure 5A
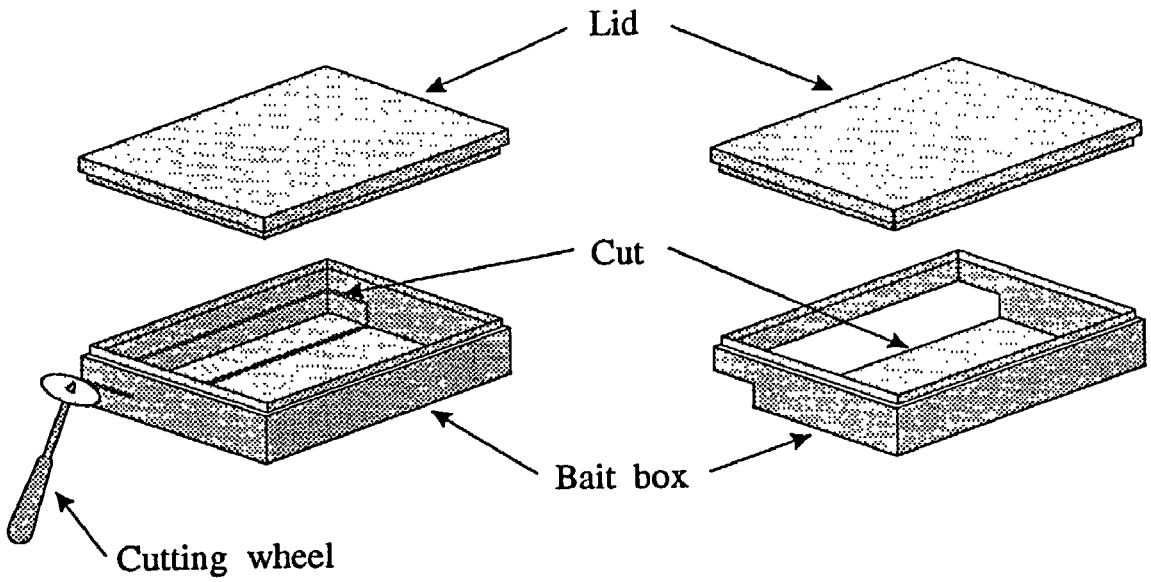
Figure 5B
Figure 5C
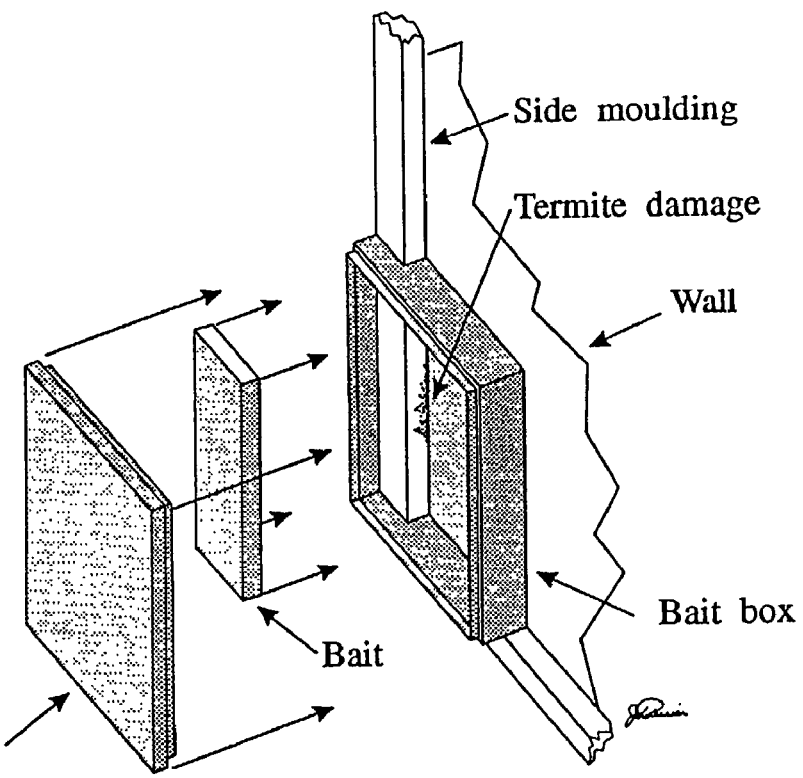

REMOTE MONITORING SYSTEM FOR DETECTING TERMITES

This application is a continuation of U.S. patent application Ser. No. 08/467,552, filed Jun. 6, 1995 and now U.S. Pat. No. 6,397,516, which is a continuation of U.S. patent application Ser. No. 08/323,582, filed Oct. 17, 1994, which is a continuation of U.S. patent application Ser. No. 08/062,868, filed May 17, 1993, abandoned, which is a continuation-in-part of U.S. patent application Ser. No. 07/975,317, filed Nov. 12, 1992, abandoned, which is a continuation-in-part of U.S. patent application Ser. No. 07/891,896, filed Jun. 1, 1992, abandoned.

BACKGROUND OF THE INVENTION

Subterranean termites most often enter structures from the surrounding soil to feed on wood, or other cellulosic material, of the structure and its contents. If unchecked, termites can cause considerable damage. As a result, efforts to erect physical or chemical barriers to prevent the entrance of termites into a structure or to exterminate the termites after they have invaded a structure have proven a considerable expense to the public (Su, N. Y., J. H. Scheffrahn [1990] *Sociobiol.* 17(1): 77-94). The cost to control termites in the United States exceeds one billion dollars annually (Mauldin, J. K, S. C. Jones, R. H. Beal [1987] The International Research Group on Wood Preservation Document No. IRG/WP/1323).

Subterranean termites construct an extensive foraging gallery beneath the soil surface. A single colony may contain several million termites with foraging territory extending up to 300 feet (Su, N. Y., R. H. Scheffrahn [1988] *Sociobiol* 14(2):353-359). Since subterranean termites are a cryptic creature, their presence is not normally known until after some damage, foraging tubes, or live termites such as swarmers, are found. Some subterranean termites are known to forage beneath an object on the soil surface (Ettershank, G., J. A. Ettershank, W. G. Whitford [1980] *Environ. Entomol* 9:645-648).

Currently, there are two basic approaches for the control of subterranean termites: preventive control and remedial control. In some of the United States, it is mandatory that the soil underlying the foundation of newly constructed buildings be pre-treated with a pesticide (also referred to herein as termiticide) to prevent termite infestation. Pesticide is typically sprayed over and into the soil prior to construction. This pre-construction treatment produces a horizontal barrier beneath the building. Because of the lack of communication between pesticide applicator and construction workers, the barrier often loses its continuity during the construction. Moreover, the currently available soil termiticides tend to lose their biological activity after five or more years to the extent that the treated soil is no longer effective against termite invasion. Established termite colonies in the soil may then invade the structure if additional chemical is not applied beneath and around the structure.

When a house or other building is infested by subterranean termites, efforts are made to create a continuous barrier beneath the building in the soil where the subterranean termites are provided access to the building. A common method of creating this barrier is to introduce termiticide around a building foundation by injection into soil underlying concrete foundations, drenching the soil surrounding the building perimeter, or a combination of both. This type of post-construction treatment is labor-intensive and may not adequately produce a continuous barrier (Frishman, A. M., B. L. Bret [1991] *Pest Control* 59(8):48, 52, 54, 56; Frishman, A. M., A. St. Cyr [1988] *Pest Control Technology* 16(4):33, 34, 36).

Other remedial treatments include spot treatments such as dusting or injecting termiticides within the walls of the building. Robert Verkerk has described arsenic trioxide dust treatment using termite lures (Verkerk, R. [1990] *Building Out Termites*, Pluto Press Australia Limited, P.O. Box 199, Leichhardt, NSW 2040). Verkerk describes the use of stakes or blocks of termite susceptible timber to lure termites after the stakes or blocks have been placed near a known termite problem. Once termite activity is observed, arsenic trioxide is injected. Alternatively, a portion of the termites may be dusted with arsenic trioxide.

Most spot treatments are done to stop existing termite infestations at a particular area in a structure but generally affect only a small portion of the subterranean termite population, i.e., those termites which come into direct contact with the pesticides. Because of the extensive foraging populations and expansive territory of subterranean termite colonies, the vast majority of the termite population is not affected by such spot treatments.

U.S. Pat. No. 3,940,875 describes a method, however impractical, for dispensing termite poison in the soil in an attempt to extend the life of the barrier type treatment such that the presence of termites is signalled by the release of an odor when the termites feed on the poison. The '875 patent also describes a termite-edible container which gives off an odor when eaten by a termite. In addition to the '875 patent and the Verkerk article referenced above, other publications describe the use of termite-edible materials as components of schemes to control termites. For example, Japanese patent application Nos. 61-198392 and 63-151033 describe wooden vessels specifically designed to "attract" termites as part of a monitoring procedure. The 61-198382 application describes a vessel preferably made from pine or cedar, used in an attempt to attract termites. The 63-151033 application also uses a wood attractant to entice termites. In the 63-151033 application, the termites are further exposed to a toxicant which is then presumably carried back to the nest in hopes of killing the queen via trophallaxis or food exchange. Neither Japanese application provides any data establishing that the described process actually has any impact on termite populations. Furthermore, there is no indication that it is possible to "attract" termites at all. These methods have further important disadvantages. For example, the wooden inducing body will be subjected to fungal decay before termite attack, especially in moistened soil Thus, frequent replacement of the inducing body is needed during the monitoring period. Further, damage to the inducing body can result in the penetration of the termiticide into the ground. This is not environmentally acceptable.

One termite control method comprises placing a highly toxic material, such as an arsenic-containing dust, at a site of infestation in the hope that this will directly control an effective number of termites at the site and also other termites back in the colony. However, this method relies on pumping toxic dust into a termite tunnel and depositing relatively large quantities of dust.

Elaborate schemes of pipes to convey liquid termiticides under and surrounding buildings have also been proposed for termite control. It has been suggested that these liquid termiticides may be dispensed into the soil surrounding and below the building through these pipes to provide a continuous barrier to the incursion of termites. This method requires a large quantity of termiticides in order to saturate the soil surrounding the building.

U.S. Pat. No. 5,027,546 describes a system intended for use on above ground termites, i.e., drywood termites, which controls termites by freezing with liquid nitrogen. Although the liquid nitrogen is essentially non-toxic in that no toxic residues persist, it is hazardous to use and the method is a spot treatment and will not affect the majority of termites. U.S. Pat. No. 4,043,073 describes a method which attempts to circumvent the problem of repeated application of pesticide. The described method functions by "encapsulating" the insecticide, thus making it more persistent. The overt use of pesticides and their persistence in the environment are not remedied by this system. Another proposed system which fails to alleviate the problem of transferring insecticide directly into the soil is U.S. Pat. No. 3,624,953. This method employs a reservoir of insecticide wherein the vapors of the insecticide are permitted to permeate the soil surrounding the reservoir. Thus, exposure of the environment with toxic substances is not avoided by using this method.

Toxicants which have less environmental effect and which show activity against termites are known (Su, N.Y., M. Tamashiro, M. Haverty [1987] *J. Econ. Entomol.* 80:1-4; Su, N.Y., R. H. Scheffrahn [1988] *Florida Entomologist* 71(1): 73-78; Su, N. Y., R. H. Scheffrahn [1989] *J. Econ. Entomol.* 82(4):1125-1129; Su, N.Y., R. H. Scheffrahn [1990] *Sociobiol.* 17(2):313-328; Su, N.Y. [1991] *Sociobiol.* 19(1):211-220; Su, N.Y., R. H. Scheffrahn [1991] *J. Econ. Entomol.* 84(1):170-175; Jones, S. [1984] *J. Econ. Entomol.* 77:1086-1091; Paton, R., L. R. Miller [1980] "Control of *Mastotermes darwiniensis* Froggatt (Isoptera: Mastotermitidae) with Mirex Baits," *Australian Forest Research* 10:249-258; McHenry, W. E., U.S. Pat. No. 4,626,528; Henrick, C. A., U.S. Pat. No. 5,151,443). However, none of these toxicants have previously been used in conjunction with a method which efficiently and efficaciously delivers the toxicant to a target pest.

Australian Patent No. 1,597,293 (the '293 patent) and a corresponding Great Britain Patent, No. 1,561,901, describe a method which involves mixing insecticide with a food matrix comprising cellulose and a binding agent. The method described in the '293 patent relies on the termite ingesting the insecticide along with the matrix, then returning to the colony to introduce the insecticide to other termites through the natural process of trophallaxis (food exchange between termites). However, the '293 patent describes usages only when termites are known to be present and, furthermore, the described method fails to ensure that the termites will initially find the matrix and relies on those termites finding the matrix to transfer sufficient amounts of the insecticide to the colony solely by trophallaxis. Like the Japanese patent application No. 63-151033, the method of the '293 patent requires that the matrix is more attractive to the termites than surrounding materials. The method described in the '293 patent relies on the moisture in the matrix (supposedly retained by the binding agent, agar) to attract termites. The described method, therefore, is primarily for termite species that are attracted to moisture (or those under "water stress"). Moreover, the '293 method fails to assure that the moisture will remain in the baits when applied in the field awaiting termite arrival. This is an unrealistic requirement for a practical application, because even a moistened sawdust-agar matrix will desiccate within a few days when placed in a dry soil.

It should be noted that attractants other than water for termites have been investigated. For example, the extract from brown-rot fungi chemically resembles the trail-following pheromones of termites. Natural pheromones, however, are species-and even colony-specific. A pheromone that is "attractive" to one species or colony of termites may repel termites of other species or colonies. It is of uncertain value, therefore, to incorporate pheromone mimics (such as the brown-rot fungi extract) in a bait, especially if a bait is to be used against a wide range of termite species.

It should also be noted that trophallaxis is an uncertain means of delivering the insecticide to the colony because it assumes that digestive enzymes and other metabolic processes do not affect the active ingredient. However, once the insecticide is ingested by the termite, the insecticide may be rendered inactive by the digestive process of the termites. Moreover, suppression of a termite population requires that a substantial number of termites in the colony are disabled before their damage potential is diminished Relying only on trophallaxis to transfer the toxicant does not ensure that adequate numbers of termites will be controlled.

Modifications to the method described in the '293 patent may not increase the bait intake of termites. For example, the '293 method requires that the matrix mixture be applied at a known infestation site such as a termite mound or tree trunk. This method, therefore, can be used only as a remedial treatment. The '293 method cannot be used unless activity of termites is detected. The '293 patent also proposes that a large quantity of toxicant bait be placed at random locations as a preventative measure. However, without providing a procedure for detecting termites, the majority of this bait may desiccate or degrade due to fungal growth and become unpalatable to termites. Moreover, an unnecessarily large quantity of toxicant is applied in the environment.

It is therefore highly desirable to more effectively control termites or other insects in a manner which assures that the termites or other insects of interest are exposed to the toxicant, which minimizes environmental harm by reducing the amount of insecticide used, and which affects adequate numbers of termites in a colony.

BRIEF SUMMARY OF THE INVENTION

The invention disclosed and claimed herein relates to a method for controlling populations of pests. The invention is most advantageously used for controlling the population of social insects which communicate through chemical signals. Specifically exemplified herein are methods and devices for the control of insects of the order Isoptera, particularly, termites.

One preferred method of the subject invention is most easily thought of as comprising two steps. These two steps can be repeated to form a multistep process or the two steps can be conducted concurrently. One step involves monitoring and/or capturing target pests by a means which does not employ the use of any pesticide. This step functions to detect the presence of pests. In addition, this monitoring step can also function as a means to capture the pest without causing the pest substantial harm or disturbance of colony activity. In the embodiment of the invention wherein pests are captured, the captured pest is still alive and, preferably, capable of moving, eating, and producing chemical signals which can attract fellow pests. This step of the process, wherein the pests are detected or captured is hereinafter referred to as the "monitoring" step.

The other step of the process involves controlling a population of pests once they have been detected. The pests may have been detected, for example, as a result of the monitoring step. In the control step of the process, the pests are controlled as a result of ingesting or otherwise contacting a toxicant. The subject invention has been discovered to be highly effective in controlling even extremely large termite colonies. Advantageously, the control method utilizes only very small amounts of toxicant, and this toxicant is applied in a strictly defined and controlled manner to minimize exposure of the environment to toxicants. The use of toxicant is confined in terms of the very limited quantity and coverage of the toxicant, and in terms of the period during which the toxicant is used. Once control is attained, the monitoring step can continue. These steps can also be conducted simultaneously.

Specific carriers of toxicants, such as bait or tracking powder, are aspects of the subject invention. These carriers are referred to herein as matrices. Also described are apparatuses for presenting the toxicant-containing matrix to the target pest.

In a preferred embodiment of the invention, the control step of the process can utilize pests which have been captured in the monitoring step. Specifically, these captured pests can be used to attract or recruit other pests to the toxicant-containing matrix, herein referred to as "self-recruitment," and, in some instances, to deliver toxicant to a nest or colony of the pests. The unique use of captured pests to make the toxin matrix more attractive to nestmates is referred to herein as "self-recruitment." As described herein, a captured pest can be induced to chew or move through a toxicant-containing matrix before travelling to the nest. In a preferred embodiment of the subject invention, the toxicant is relatively slow-acting so the pest can travel through the colony territory before dying. Because the termite leaves the toxicant-containing matrix before dying, this method prevents the tainting of the carrier and vicinity of the matrix with dead or dying termites. In the course of traveling within the nest, the pest can leave a chemical trail directing or recruiting other of the target pests to the toxicant-containing matrix. Also, the captured pests can leave chemical signals in the toxicant-containing matrix itself, communicating the desirability of the food. Because these chemical markers are species- and even colony-specific, these chemicals are highly advantageous for self-recruitment of nestmates to the toxicant-containing matrix Also, the pest may deliver toxicant to the nest, for example, via trophallaxis or cannibalism, where the toxicant can kill other nestmates. The effect of this method is to make the toxicant-containing matrix much more attractive to the termites. This attractiveness can result from the highly specific trail pheromones which direct other nestmates to the toxicant-containing matrix and, more importantly, the deposit in the toxicant-containing matrix of feeding initiating pheromones which can be highly specific for the particular termite colony which is to be eliminated.

The invention also relates to materials used in carrying out the novel methods. One critical element of the subject invention is the toxicant-containing matrix which can comprise a toxicant and a binder such as Methocel®, agar, other cellulosic materials, other materials which are non-repellant to the target pest, or a combination of two or more of these components. Preferably, the toxicant is slow-acting. If a cellulosic material is used, that material may consist of wood particles. The matrix can further comprise components which stabilize or regulate the matrix environment. For example, a humectant such as a hygroscopic component can be added to regulate the moisture content of the matrix Certain novel apparatuses are also used according to the subject invention. Specifically disclosed are apparatuses for monitoring and controlling populations of insects, particularly termites. For example, one such apparatus for monitoring the presence of termites simply comprises a food source as a monitoring device which can be strategically placed at sites surrounding a structure, or at an agricultural location. These monitoring devices are accessible to the pest management operator or property owner so that they can be periodically monitored for evidence of the presence of termites. Other apparatuses, such as electronic devices, can be incorporated in the monitoring devices to alert the homeowner or pest control operator to the presence of termites. Where ground or soil surrounds a structure to be monitored for termites, the monitoring device can be placed in the soil near the structure or area to be monitored. Where no soil is around a structure or when foraging galleries are detected above ground, the monitoring device or toxicant-containing matrix can be placed above ground. Advantageously, the monitoring device can be constructed so that pests can be removed easily and without substantial harm resulting to the pest, thereby allowing the pest to be used to recruit other nestmates to the matrix Another apparatus useful according to the subject invention comprises a housing which is specifically designed to enclose either a monitoring device or toxicant-containing matrix This housing is useful for protecting the monitoring device and/or toxicant-containing matrix from the environment. The monitoring device or matrix can be enclosed within the housing in such a manner so they can be removed with minimal disruption to the foraging termites. This housing is preferably made from a durable, non-biodegradable material The present invention provides an environmentally safe termite control system requiring no complex machinery. The invention provides apparatuses and methods for the monitoring of, and delivery of a toxicant to, a target pest wherein the apparatuses may be easily and safely serviced by property owners as well as professional pest management workers.

Advantageously, the disclosed materials and procedures minimize the risk of exposure to persons handling toxicants and increase toxicant intake by termites. The methods of the subject invention can drastically reduce pesticide use in the urban environment. Moreover, this invention can be an important part of an Integrated Pest Management (IPM) approach. The first phase of the IPM can be designed to monitor termite activity. No pesticide need be used until termite activity is detected. When activity is detected, the second phase of the IPM can be employed wherein only a small quantity of pesticide is used to control the entire colony population. Once control is achieved, the monitoring step can be repeated, as can the control step, if necessary, thus providing indefinite protection to the structure or agricultural site.

As described more fully herein, there are a variety of methods and apparatuses which can be utilized to practice the method of the subject invention. The precise methods and apparatuses which would be optimal for a particular target pest and environmental setting would be apparent to a person skilled in this art using the teachings provided herein.

The descriptions and teachings which follow primarily focus on the control of termites. Specific methods and apparatuses for the control of termites are provided, but variations of these methods and apparatuses and their applicability to pests other than termites would be readily recognized and used by a person skilled in this art.

BRIEF DESCRIPTION OF THE DRAWINGS

FIG. 1a shows placement of the monitoring device into a station prepositioned in the soil and placement of a cover over the station; FIG. 1b shows termite foraging tunnels which lead to the station and the monitoring device; FIG. 1c shows removal of the monitoring device and replacement with a toxicant delivery tube within the same station; and FIG. 1d shows that the termites captured in the monitoring device are placed into the recruiters' chamber of the toxicant delivery tube to recruit other termites to the toxicant.

FIGS. 5a-5c show one example of an termite monitoring/capturing/toxicant-delivery station. FIGS. 5a and 5b show a section cut out for placement against a wall having a molding. FIG. 5c shows an exploded view of the box, toxicant matrix, and lid as appropriately mounted against a wall.

DETAILED DISCLOSURE OF THE INVENTION

Figure 1A:
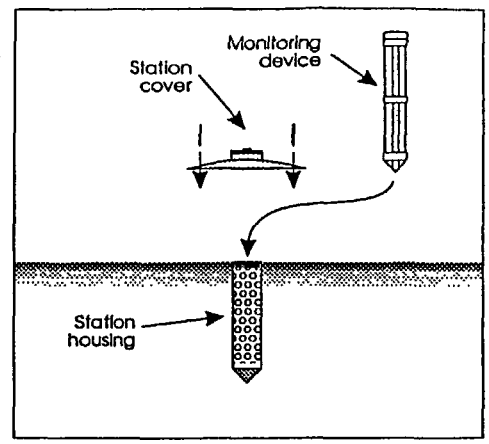
FIGS. 1a-1d illustrate one embodiment of the invention wherein a single station housing is used to house a monitoring device and then a toxicant delivery tube. Specifically.
Figure 1B:
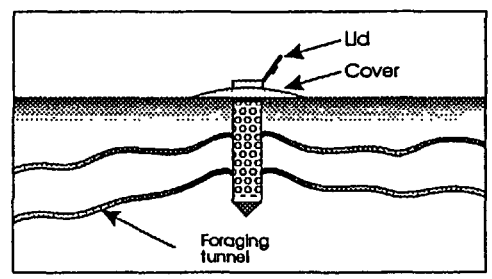
Figure 1C:
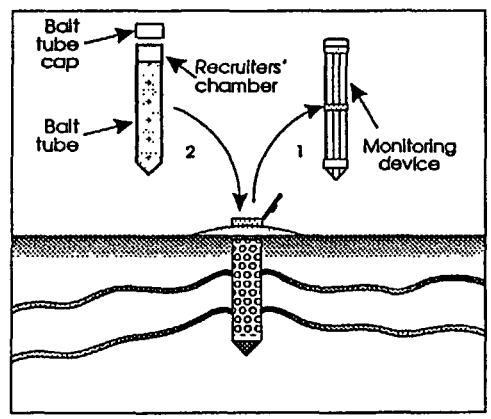
Figure 1D:
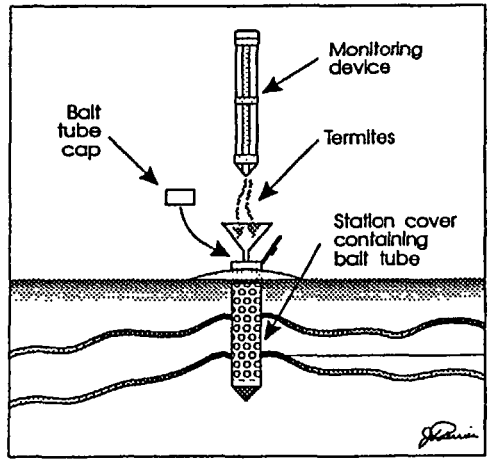

The subject invention pertains to novel methods and apparatuses for controlling populations of pests. The present invention is based on the concept of providing a suitable toxicant in a matrix which is non-repellant to the species of pest to be controlled. In a preferred embodiment, the invention further comprises a self-recruiting method of bringing additional pests to the toxicant. As described in detail herein, the self-recruiting aspect of the subject invention is a very unique and effective means of making a toxicant-containing matrix much more attractive to the pests from a specific colony which is to be eliminated. Thus, a very important aspect of the invention is a means for making a toxicant more attractive to pests, particularly pests from a specific nest or colony.

The described method is most readily applicable to insects which live in colonies and which communicate by chemical signals such as, for example, pheromones. Pheromones are naturally produced chemotactic compounds that termites and other insects are known to use as communication signals. The described method can be used, for example, to capture and control insects of the order Isoptera, and is particularly useful for controlling populations of subterranean termites. It would be readily apparent to persons of ordinary skill in the art that the method and apparatuses are adaptable to a variety of pest species. Examples of termite species which can be controlled by use of the disclosed method include *Coptotermes formosanus, Reticulitermes flavipes, R. hesperus, R virginicus, R tibialis*, and *Heterotermes aureus*, as well as termite species of the families (and pest genera) Mastotermitidae (*Mastotermes* species), Hodotermididae (*Anacanthotermes, Zootermopsis* species), Rhinotermitidae (*Coptotermes, Heterotermes, Reticulitermes, Psammotermes, Prorhinotermes, Schedorhinotermes* species), Kalotermitidae (*Glyptotermes, Neotermes, Coptotermes, Incisitermes, Kalotermes, Marginitermes* species), Serritermitidae, and Termitidae (*Pericapritermes, Allodontermes, Microtermes, Odontotermes, Nasutitermes, Termes, Amitermes, Globitermes, Microcerotermes* species), Termopsidae (*Hodotermopsis, Zootermopsis* species), and other pest species of termites. For purposes of brevity, the emphasis herein is directed to subterranean termites.

A preferred embodiment of the invention features two repeatable steps: (1) population monitoring/capturing (hereinafter referred to as monitoring), and (2) delivery of a toxicant to a pest through the use of a toxicant-containing matrix. The monitoring step of the process comprises monitoring a particular location to detect any termite activity. This step may further comprise capturing termites. The toxicant delivery step involves providing a slow-acting toxicant in a matrix which is eaten or otherwise contacted by the termites. The slow-acting toxicant allows termites to return to and move through their colony territory before dying. Nestmates then follow the trail back to the toxicant. As described more fully herein, the two principal steps of the subject invention can be repeated as part of a pest management program wherein the program involves the initial step of monitoring for pest activity followed by control if pest activity is observed. Once control is achieved, monitoring can be continued. The steps may also be performed simultaneously. Also, an initial monitoring step may not be necessary if termite activity has already been detected. In a preferred embodiment, a single station housing, as described herein, is used for both monitoring and control This station housing is a unique containment device which is made of a durable, non-biodegradable material which permits long-term monitoring and repeated cycles of monitoring and control.

Each of the two above-referenced steps is described in more detail below. Also discussed below in greater detail is the self-recruitment aspect of the toxicant delivery step. Also discussed in greater detail below are specific apparatuses useful according to the subject invention.

A Monitoring. The primary objective of the monitoring step is to detect the presence of subterranean termites and not to attract termites from other locations. If termites are present, this step provides an opportunity to collect them. If termites are collected, these termites can then be used for recruiting other nestmates to a toxicant according to the toxicant delivery step of the invention. Therefore, it is preferred that termites be collected in a manner which does not adversely affect the termite's viability. The terms "without affecting viability" and "remain viable" mean that the captured termite is relatively unharmed and that it is able to forage and, preferably, has sufficient mobility to return to the nest.

Certain devices can be used to monitor for termite activity. These devices are described in greater detail below. The monitoring devices can be placed in, on, or above the ground. These devices may be placed individually or interconnected to surround structures to be monitored. The materials used for the monitoring device should not repel or deter termites. Preferably, these materials should have sufficient structural integrity to exist in variable environments (high humidity, aridity) for a period sufficient for termites to locate and access the monitoring devices. The monitoring device should be able to withstand foraging activity by a large number of termites so the device is not totally consumed within a reasonable time interval between inspections.

In a preferred embodiment of the monitoring step, an article can be both used to detect and capture the target termites. The article is, thus, the "monitoring device," or "monitoring article." The device employed in this monitoring step preferably allows the capture of termites with a minimum amount of harm to the termites. The device can be of any material which is susceptible to termite infestation. Preferably, the material comprises cellulose.

One preferred embodiment of the monitoring step utilizes an outer housing which is separate from but surrounds the monitoring device. The outer housing is also referred to herein as the station housing. In a preferred embodiment, the station housing can have a plurality of entry points which allow termites access to the monitoring device. These entry points must be large enough to allow entry of the target pest and can be much larger. The station housing can further comprise a reinforced tip at one end to facilitate placement into the ground. The station housing may further comprise, at the end opposite the reinforced tip, a cover. The cover is described more fully below. The station housing for horizontal placement in the soil or above ground placement is also described below.

When a station housing is used, the same station housing can be used for both the monitoring step and the toxicant delivery step. For example, once termites are observed in the monitoring step, the monitoring device (without toxicant) can be removed from the station housing and replaced with a toxicant-containing matrix. One advantage to the use of the station housing is that the termite foraging tunnels will not be greatly disrupted by removal of the monitoring device if the station housing remains in place. Thus, when the monitoring device is replaced with a toxicant-containing matrix, foraging can commence readily without extensive restructuring of the foraging tunnels of the termites. Furthermore, once control of the termite population has been achieved using the toxicant-containing matrix, the toxicant-containing matrix can be readily replaced with a monitoring device to resume monitoring of the location. Throughout the process, the station housing can remain in place. Thus, the station housing is preferably made from a durable, non-biodegradable material and becomes a critical component of the pest management program.

The monitoring device or, preferably, the station housing containing the monitoring device, can be placed in the ground or other appropriate location for a time sufficient to allow termite infestation. The monitoring device can be placed in the ground directly by being driven into the soil or placed into a pre-existing hole or location of sufficient dimension to allow the device to remain in position. Alternatively, the monitoring device can be placed inside the station housing which is placed on or in the ground. The monitoring device and/or station housing may lie flat on the ground or be placed upright in a hole.

In one embodiment of the monitoring step, the monitoring device is modified chemically and/or physically to increase the possibility that the target pest will enter and move within the device. A variety of chemical means, such as food, moisture, dry rot fungus, and pheromones or their mimics (e.g., glycol compounds), and physical characteristics, such as shape, size, and texture, can be used to achieve this objective. One example of a physical modification would be a cover placed over the station housing, or over the monitoring device if the monitoring device is used in the ground without the station housing.

Once infested by termites, the monitoring device can be gently removed from the soil or from the station housing. As stated above, it is advantageous to utilize a station housing to minimize disruption to foraging tunnels. Upon removal of the monitoring device, a toxicant-containing matrix can then be placed in the station housing or other location previously occupied by the monitoring device. In this way, toxicant is not used until the presence of termites is determined by the monitoring step.

In a preferred embodiment described more fully below, termites collected in the monitoring step are used to recruit more termites to the toxicant. This is termed "self-recruitment." Therefore, the monitoring device can be specifically designed to facilitate capture of termites. Such a device, as described below, may have interfacing sides. After removal from the ground or the station housing, the interfacing sides of the monitoring device are separated and termites extracted from them. The dimensions and shape of the monitoring device are designed so that termites foraging in the device can be extracted with minimum harm. "Minimum harm" means that the termites which are captured remain viable and are capable of foraging and producing pheromone and, preferably, are able to return to the nest for recruiting nestmates. The extracted termites are then used to recruit other termites from the colony to, and through, a toxicant-containing matrix. Termites foraging in the monitoring device can be transferred to a toxicant delivery device by gently removing or tapping them from the monitoring device into the toxicant delivery device. The toxicant-delivery device is also referred to herein as a "bait tube." The toxicant delivery device can comprise a chamber above the toxicant-containing matrix into which the termites are placed. This chamber is referred to herein as a recruiters' chamber. To exit the bait tube and station housing, the termites must then tunnel through the toxicant-containing matrix.

B. Toxicant delivery. The objective of the toxicant delivery step is to induce as many pests as possible from a colony to contact or eat a toxicant. The details of the toxicant delivery step are herein described as pertaining to termites, particularly. However, as stated above, the method can also apply to other insects, especially those social insects which live in colonies or nests and which communicate by chemical signals, i.e., pheromones.

The essential elements of a toxicant delivery system comprise the presentation of an active ingredient (AI) and a suitable carrier (matrix) in a manner that induces the target pest to ingest or contact the AI. The toxicant-containing matrix should be delivered in, on, or above the ground in a manner which minimizes exposure of the environment, applicator, and other non-target organisms to the toxicant. For example, a suitable matrix can be a coatable, suspendable, impregnable natural or artificial food source. The matrix does not need to attract pests, but should not repel them. The presentation of the matrix (in a station housing, etc.) may induce pests to contact the toxicant. The suitable matrix further can be capable of being formed into a desired shape for placing or packing into a station housing.

In a preferred embodiment for a non-rigid matrix, the toxicant-containing matrix is placed within a casing. This casing is different from the station housing and, in fact, facilitates easy placement of the toxicant-containing matrix into the station housing. Although the toxicant-containing matrix and surrounding casing are preferably placed into a station housing, the casing can, alternatively, be made of sturdy material for placement directly into the soil. The casing is necessary because, in a preferred embodiment, the toxicant-containing matrix has a very high moisture content and is somewhat amorphous and therefore needs a casing to hold its shape. The casing also helps to prevent desiccation, and it minimizes contact with the toxicant by the handler and facilitates easy removal of the toxicant-containing matrix when the toxicant delivery step is completed. Furthermore, as described more fully below, the casing can be designed to include or form a recruiters' chamber. The casing must permit entry by the target pest; therefore, the casing must either comprise appropriate openings or be of a material through which the pests chew or otherwise create an opening. For example, thin polymeric materials may be used to enclose the toxicant-containing matrix The toxicant-containing matrix can be enclosed within the casing somewhat like a sausage within its casing. The use of a polymeric material is particularly advantageous if that material is of a nature such that it prevents or delays desiccation of the matrix Other materials which can be used to encase the toxicant-containing matrix include, but are not limited to, cardboard and other cellulose materials, even paper and wax. This method for packaging the toxicant-containing matrix has the advantage of creating a "dose-pack" which precisely provides the appropriate amount of toxicant in a manner which minimizes contact with humans or the environment.

Suitable matrices can be formable cellulose-containing materials including, but not limited to, wood particles or wood flour, recycled paper or cellulose ethers such as methylcellulose, hydroxypropylmethylcellulose, and hydroxybutylmethylcellulose, commercially available under the tradename of Methocel® (trademark of the Dow Chemical Company). A preferred cellulose-containing matrix is sawdust or wood flour which is not repellent to target termite species. For use with termites and other pest species which are attracted to, or reliant on, the presence of sufficient moisture, the matrix can further comprise a humectant for maintaining moisture content An appropriate humectant can have hygroscopic characteristics. The monitoring step and toxicant delivery step could use the same matrix, except that no toxicant is impregnated into the matrix used for the monitoring step.

The preferred active ingredient should be slow-acting, lethal at concentrations which do not repel target insects, and capable of being combined with the matrix as described above. It is intended that pests directly-contacting or ingesting the toxicant will not be killed immediately but will travel to and/or through their colony to recruit other nestmates to the toxicant, thereby resulting in the control of large numbers of colony members. The term "delayed lethal effect" in the present specification means that death does not occur immediately or within a short time such as a few seconds or minutes after ingestion or contact of the active ingredient by a termite. Rather, it is preferred that the pest die hours or, more preferably, days or weeks after encountering the toxicant. This delayed lethal effect permits the termites to interact with the colony before death occurs, thus allowing the location of the toxicant delivery system to be communicated to nestmates within the colony. It is preferable that the communication be effected by pheromones because these chemical signals are a highly efficient means of communication, often being specific to a particular species or colony. In addition, communication by pheromones is enhanced according to the subject invention by the deposit directly into the toxicant-containing matrix of feeding-initiating pheromones. These pheromones are deposited by the captured pests which are forced to forage through the toxicant-containing matrix before exiting the toxicant-delivery device and/or station housing to return to the colony. This unique self-recruitment procedure results in a highly efficient process of recruiting nestmates to the toxicant matrix, ensuring their exposure to the slow-acting toxicant.

The active ingredient can comprise chemical insecticides, insect growth regulators, or microbial pathogens or their toxin preparation. Examples of toxicants include, but are not limited to, borates (boric acid, disodium octaborate tetrahydrate), mirex, sulfluramid and related fluoroalkyl sulfonamides, hydramethylnon, avermectin, A-9248 (diiodomethyl para-tolyl sulfone), fluorosulfonates, imidacloprid, azadirachtin, cyromazine, juvenile hormones (JHs), juvenile hormone analogs (JHAs), or juvenile hormone mimicries (JHMs) such as methoprene, hydroprene, triprene, furnesinic acid ethyl and alkoxy derivatives, pyriproxyfen (Nylar), fenoxycarb, and chitin synthesis inhibitors (CSIs) such as hexaflumuron and other acyl ureas, diflubenzuron (Dimilin), and azadirachtin. Biological control agents which can be used as the "toxicant" include, but are not limited to, entomogenous fungi such as *Metarhizium anisopliae* and *Beauveria bassiania*, entomogenous nematodes such as *Neoplectana carpocapsae*, insect viruses, pathogenic bacteria such as *Bacillus thuringiensis, Aspergillus flavus*, and *Serratia marcescens*, or the toxin preparations derived from *B. thuringiensis* or other biological control agents.

In addition, other insecticides can be used as microencapsulated formulations. Microencapsulation can slow the activity of otherwise fast-acting toxicants.

An example of the invention disclosed herein uses hexaflumuron, which can be impregnated or incorporated into the cellulose material during the formulation of the toxicant-containing matrix.

As discussed above, a novel feature of one embodiment of the subject invention comprises a "self-recruiting method" to use collected termites to recruit other nestmates to the toxicant. It is widely recognized that certain insects utilize chemical signals such as pheromones, which can be deposited along a trail by an insect which has located, for example, a food source. Subsequently, other insects, usually from the same colony, detect the chemical signal and are thus directed to that food source. Such trail-following pheromones of some subterranean termites have been identified; however, synthesis of such natural products or their analogs is difficult, costly, and impractical. Moreover, the proper concentration and composition of these pheromones can be species- and colony-specific. Additionally, trail pheromones may be very different from feeding-initiating pheromones. Insects are very reluctant to eat their trail pheromones because consumption of trail pheromones would remove the markers termites need to locate food sources and nestmates. Thus, it is likely that the incorporation of trail pheromones, or their analogs, into a toxicant may well act to bring termites to a location but may inhibit feeding at that location. Feeding behavior may be triggered by different pheromones which would be expected to be specific for particular pests and particular colonies. Therefore, reproducing functional synthetic pheromones would be nearly impossible for the desired purpose of widespread use in attracting termites and initiating their feeding.

An advantageous feature of the "self-recruitment" embodiment of the subject invention is to utilize a captured target pest to produce the species- and colony-specific pheromone for recruiting other pests to-the toxicant and initiating feeding behavior. This method makes the toxicant highly attractive compared to other known methods and toxicants. The method is particularly well suited for aggregating a great number of pests from a single colony to a toxicant. In accordance with the self-recruitment embodiment, termites collected in the monitoring phase are placed in the toxicant-delivery device with toxicant-containing matrix and must chew or move through the toxicant-containing matrix before returning to their nest. In this manner, the termite ingests or contacts the toxicant and leaves appropriate communication signals throughout the toxicant-containing matrix, which encourages other nestmates to locate the toxicant-containing matrix and initiate feeding activity.

Figure 3:
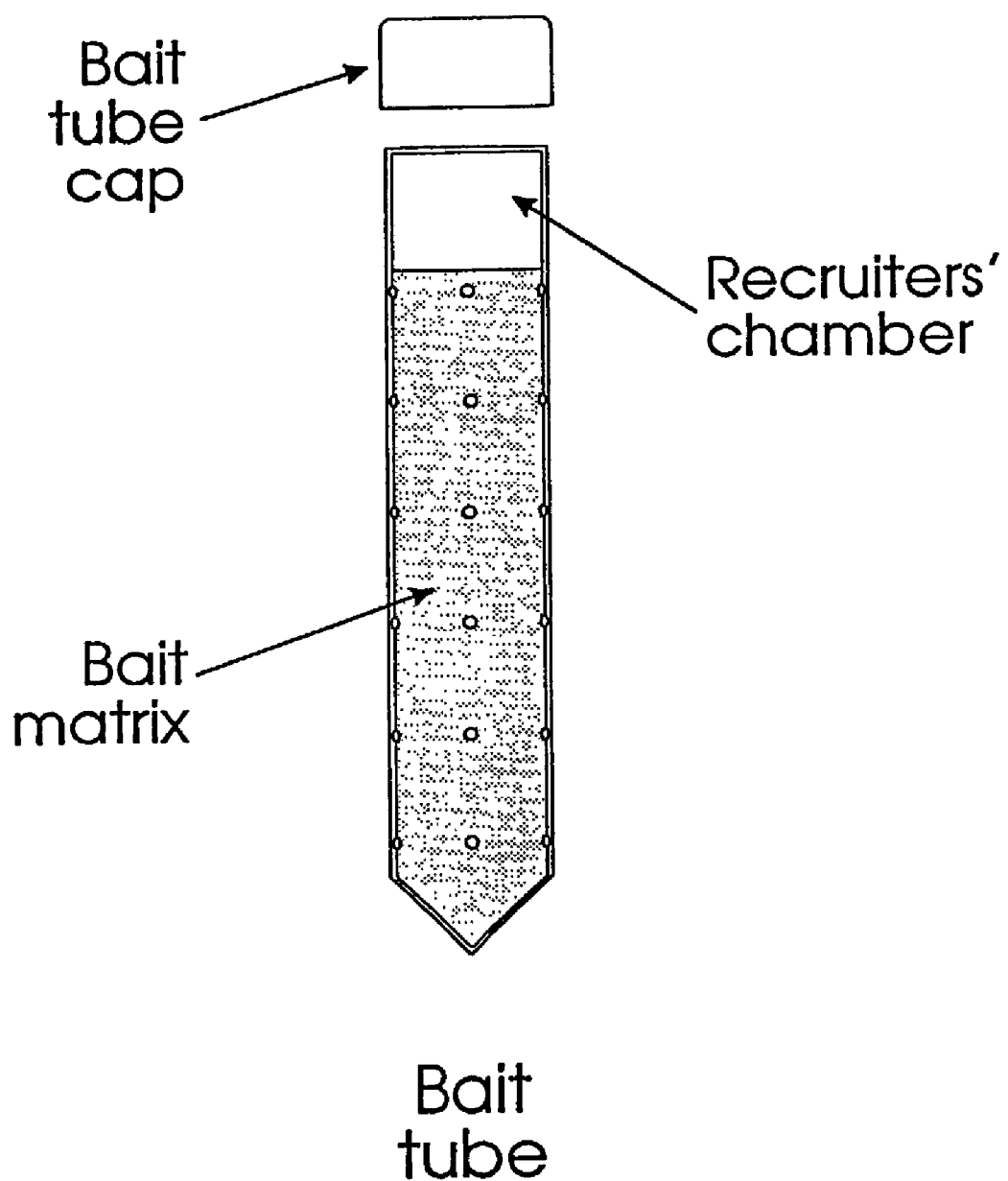
FIG. 3 shows a bait tube with recruiters' chamber.

In one embodiment of the self-recruiting system, termites in the monitoring devices are gently tapped into an empty chamber (the recruiters' chamber) situated at the top of the toxicant-containing matrix (FIG. 3). This chamber may be, for example, about 3.0 cm in diameter and about 2.0 cm deep. Smaller or much larger chambers could also be used. The open end is then preferably closed or capped. Small holes can be provided to allow air flow for termites into the recruiters' chamber. These termites must then enter the toxicant-containing matrix in order to exit the toxicant-delivery device and station housing. Holes from the recruiters' chamber into the matrix can be supplied to encourage this process. The termites then tunnel through the toxicant-containing matrix before returning to their galleries, thereby leaving species- or colony-specific pheromones in the toxicant-containing matrix. The exiting process may be encouraged by holes leading out of the matrix. This arrangement forces termites to move through the toxicant-containing matrix and thus leave favorable pheromones in the matrix and/or station housing to recruit nestmates into the toxicant-containing matrix. As discussed above, the self-recruiting procedure advantageously uses nestmates to leave the species- and colony-specific pheromones to recruit others from the same colony. This is much preferable to the use of synthetic pheromones which can fail because of their lack of specificity or because of their initiation of trailing rather than feeding behavior. The deposit of specific pheromones in the toxicant-containing matrix by the captured termites thus aids in recruiting other nestmates to the toxicant-containing matrix, whereupon they forage, are exposed to toxicant, and deposit more pheromone, thus creating a cyclical, self-recruiting termite control method.

C. Apparatuses. Employed at each step of the method of the subject invention are novel apparatuses. As described above, one method for the monitoring step employs a novel, separable article placed into the ground (or into a housing) for monitoring and capturing termites indigenous to an area. The termites are captured in such a way so that they remain viable and can be easily transferred to the toxicant delivery device used in the toxicant delivery step.

Figure 2A:
FIG. 2 shows a side and top view of a monitoring device and a station housing.
Figure 2B:
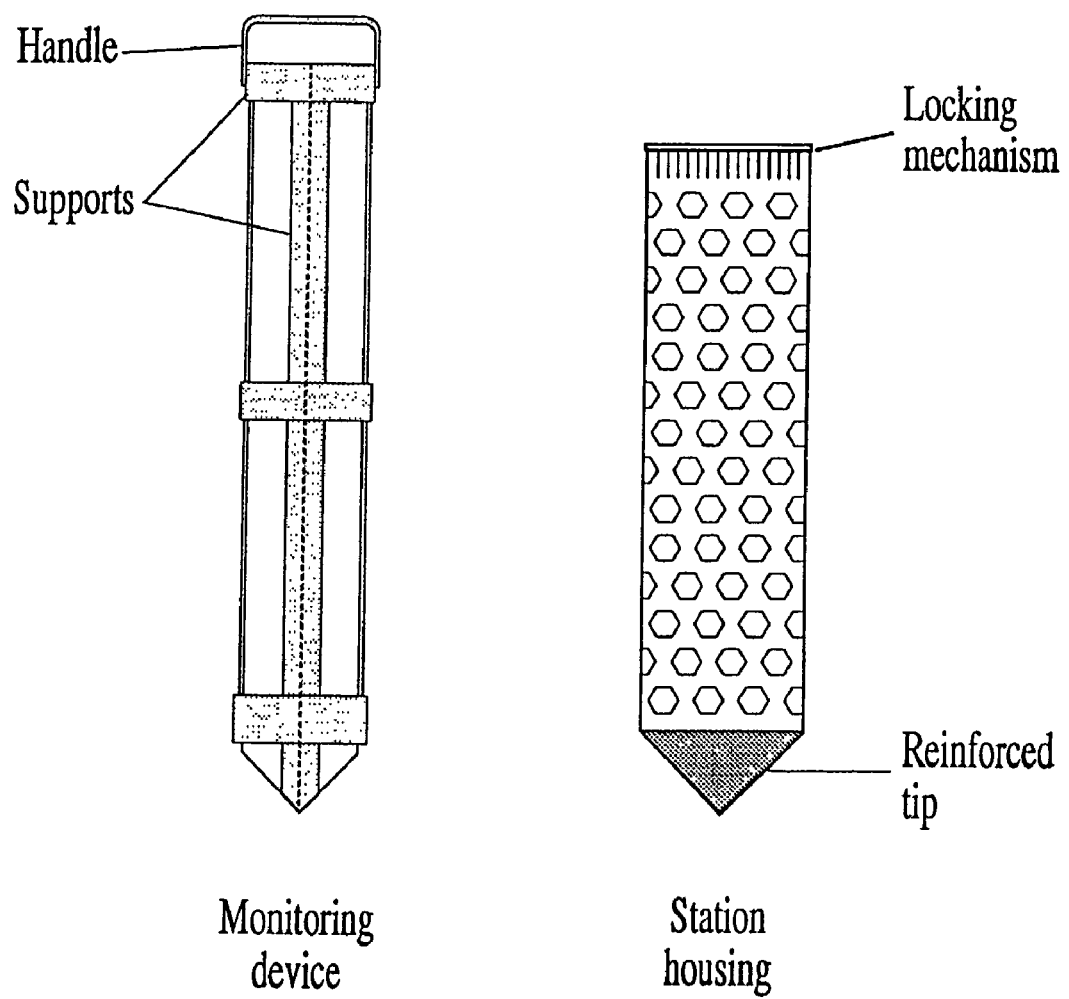

The monitoring device used in the monitoring/capture step can be comprised of at least two interfacing, separable pieces which can be bound together. The two-piece construction allows for easy collection of termites within the device. For example, a wooden stake can be comprised of two or more interfacing pieces which are bound together. The binding which holds together the pieces can be flexible metal bands, an adhesive tape, or the like. As shown in FIG. 2, the interfacing pieces can be enclosed within a bracket device comprised of horizontal bands which are interconnected by longitudinal supports which form a bracket and which further has a handle at one end to facilitate removal of the monitoring device from the ground even when badly damaged by the termites.

Alternatively, for monitoring above-ground, an apparatus which houses a food source such as sawdust, or a modified monitoring device, can be placed on or attached to (or inside) a tree or the wall of a structure. The above-ground monitoring device is also easily accessible for periodic monitoring and capture of pests for use in the toxicant delivery step.

The monitoring and toxicant delivery steps employ novel housing apparatuses. The novel housing apparatuses, or station housings, of the subject invention are designed to protect and enclose the monitoring device and toxicant-containing matrix and, preferably, to encourage termites to contact the toxicant-containing matrix wherein the termites are exposed to lethal doses of a slow-acting toxicant.

One embodiment of the subject invention can utilize a single station housing which can house the monitoring device for use in the monitoring step and then, after removing the monitoring device, can also house the toxicant-containing matrix. Alternatively, the station housing may be designed to simultaneously hold both the monitoring device and the toxicant-delivery device. When the monitoring step employs sawdust or other cellulose-containing material as a component of the monitoring device, the sawdust can be packaged in a casing for convenient placement into, and removal from, the station housing. Preferably, the material used to package the monitoring mixture can also be a cellulose-containing material such as paper, cardboard, paperboard, or the like, so that it is palatable to termites. Similarly, as described above, the toxicant and its matrix can be packaged in a casing such as a cellulose-containing package wherein the packaging serves as a barrier to prevent the handler from exposure to the toxicant.

Thus, in a preferred embodiment, the station housing is intended to remain in place indefinitely to house the monitoring device for long-term monitoring and to house the toxicant-containing matrix when necessary for control. Therefore, for purposes of the subject invention, the station housing should be durable enough to contain the monitoring device or toxicant-containing matrix (or toxicant-delivery device) in variable environments (i.e., wet vs. arid), and should be constructed in a manner, or of a material, that will allow target pests to pass through the housing, i.e., with pre-formed entry points, or of a material in which insects can form their own openings. The station housing should be non-degradable and be non-repellant to target insects. A preferred station housing is capable of repeated or continued use, is environmentally acceptable, and is an effective barrier between the toxicant and the handler or the environment. It is also capable of being removed and reused in another location. Materials from which the station housing can be constructed include, but are not limited to, polymers such as plastic, non-corrosive metal such as aluminum or stainless steel, wax, and non-biodegradable cellulose-based materials. Station housings which are not eaten by termites are preferred. The station housing can be readily adapted for above-ground use, for-example, in trees or on structures.

A non-rigid toxicant-containing matrix will typically be enclosed within another material (casing) so as to form a bait tube (also referred to herein as a toxicant-delivery device) designed to minimize direct contact of persons handling the bait tube with toxicant-containing matrix, and to allow termites collected from the monitoring procedure to return back to the foraging galley for recruiting other nestmates. The bait tube should be of a size and shape that is large enough to contain an effective amount of toxicant while still being easily handled by individuals. The bait tube should further be of a size and shape that is accessible to the target insects. The various shapes of the bait tube can include, but are not limited to, cylinders, discs, rectangles, and cones. The bait tube may be designed to be placed directly in the soil or be of a shape that allows for compatible fit into the station housing.

In a preferred embodiment, the station housing comprises a cover which not only protects the monitoring device but also performs several other important functions. Specifically, the cover may be designed so as to modulate the microenvironment surrounding the station housing. For example, the cover may advantageously be designed to extend out beyond the boundaries of the main compartment of the station housing such that the nearby ground will be covered. This has the effect of shading the surrounding soil, thus keeping the surrounding soil cool and moist in warm climates or insulating for warmth in colder climates. These conditions have been found to increase the chances that foraging termites will contact the station housing and enclosed materials. An extended cover also helps to facilitate visual location of the station housing. The cover may be secured to the soil to stabilize the entire housing as well as facilitating in the removal of the internal apparatuses used with pulling the station housing out of the soil.

To facilitate insertion and removal of the monitoring device and toxicant-containing matrix, a closeable opening (also referred to herein as the lid) may be provided in the cover.

Advantageously, the lid may be equipped with a tamper-resistant or child-resistant mechanism. In a preferred embodiment, the lid will only be removable with the aid of a tool specifically adapted for the purpose of removing such lids. The tool then would be used to facilitate inspection of the station housing. The station housing may be of one piece construction or of multi-piece construction. For example, the cover may be made as a separate piece which fits onto or over the rest of the station housing. Alternatively, the cover may be molded, or affixed to, the rest of the station housing. Similarly, the lid may be affixed to or removable from the cover and the rest of the station housing. One embodiment of the station housing is shown in FIG. 2.

One embodiment of the cover is a circular or disc-shaped device having a convex top and concave bottom side. Insulation material such as expanded polystyrene foam may be incorporated in the cover material to further maintain stable temperature and humidity beneath the cover. The cover may be, for example, four inches or more in diameter. The bottom side of the cover can be radially ribbed or grooved. The top side can be smooth-surfaced. As described above, at the center of the cover can be a closeable opening (lid). The opening can be of sufficient dimension so that the monitoring device or toxicant-containing matrix or bait tube can be passed therethrough. The lid can also serve as an inspection window. In addition, located approximately between the center and outer edge of the cover can be small holes so that nails or similar fasteners can secure the cover to the ground.

The station housing may also comprise an extractor, or equivalent device, which facilitates the removal of the monitoring device and toxicant-containing matrix (bait tube) from the station housing. The extractor may comprise, for example, handles, strings, cords, or other implement capable of directly pulling the monitoring device and toxicant-containing matrix from the station housing. Alternatively, the pulling device may be connected to a shelf upon which the monitoring device or bait tube sits. The pulling device then pulls the shelf and the monitoring device or bait tube out of the station housing. This embodiment is particularly advantageous because it enables the removal of either the monitoring device or the toxicant-containing matrix In this way any contact with the toxicant-containing matrix can be minimized. Furthermore, the activity of termites on either the monitoring device or the toxicant-containing matrix may substantially reduce or eliminate the structural integrity or rigidity of these articles, thus making them difficult to remove without the aid of an extractor which comprises a shelf component to pull out the material. A further advantage of the shelf component of the extractor is that it facilitates removal of any dirt or debris which may accumulate in the station housing over a period of time. This may be of particular importance in sandy soil. The extractor may also function to hold together the pieces of the monitoring device such that the device is in one piece when in the station housing but is easily separated into two or more pieces when removed from the housing.

In a preferred embodiment of the invention, termites captured in the monitoring step are forced to move through the toxicant-containing matrix before exiting to return to their colony. In this embodiment, the station housing or the toxicant-delivery device (bait tube), or both, are specifically adapted to force termites through the toxicant-containing matrix For example, the casing for the toxicant-containing matrix may have a rigid upper portion which extends a short distance beyond the end of the toxicant-containing matrix. This rigid upper portion is impenetrable to termites. The end of the casing is also impenetrable to termites, and the rigid upper portion of the casing, together with the end portion which is connected to the rigid upper portion, form a recruiters' chamber with the final side of the chamber being formed by the toxicant-containing matrix. Thus, to exit the recruiters' chamber, the termite is forced to move through the toxicant-containing matrix. Many different versions of this recruiters' chamber could be envisioned, readily constructed, and used, by a person skilled in the art having access to the teachings provided herein.

Following are examples which illustrate procedures, including the best mode, for practicing the invention. These examples should not be construed as limiting. All percentages are by weight and all solvent mixture proportions are by volume unless otherwise noted.

EXAMPLE 1

Integrated Pest Management System for the Control of Termites

One example of how methods of the subject invention can be applied to the control of subterranean termites is as follows:

(a) Placement of the station housing and monitoring device. A hole of appropriate dimension can be made in the soil for positioning of the station housing. The station housing is placed into the hole. The monitoring device is placed inside the station housing. A cover can be placed over the station housing and the cover secured to the surface of the ground. Alternatively, the monitoring device can be placed inside the station housing which is then inserted or hammered into the soil until the station housing opening is near the soil surface. Also, the monitoring article or station housing may be placed horizontally on the ground or beneath the soil surface.

Figure 4:
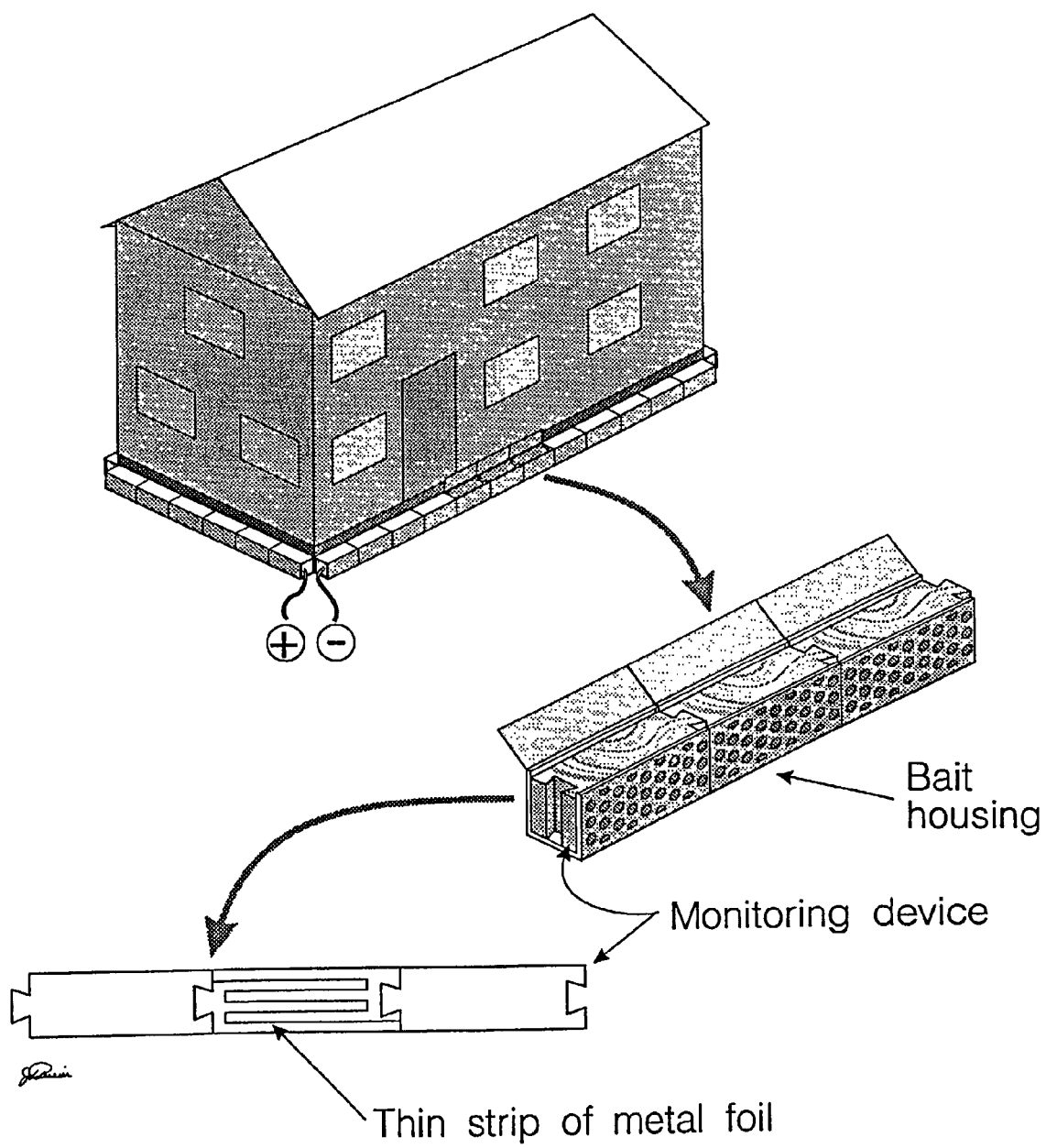
FIG. 4 shows a contiguous station housing containing monitoring blocks placed in soil adjacent to a structure foundation. A thin strip of metal foil is embedded in the monitoring block. When the monitoring blocks are connected together to surround the structure, a contiguous circuit is formed. Severe infestation by termites in the monitoring block results in the breaking of the circuit, which can be easily detected by an electronic device.

(b) Inspection of monitoring devices. The monitoring device can be inspected periodically for evidence of termite infestation by visually examining the device for signs of infestation. Inspection of the monitoring device can be performed weekly, bi-weekly, monthly, etc. as needed or desired. Inspection may be done visually, or automatic monitoring devices may be used. For example, termites are known to chew through soft metal. Therefore, thin strips of metal may be incorporated into the monitoring device and connected to an electronic device. When termites chew through the thin metal, the circuit is broken, thus evidencing the presence of termites. See FIG. 4. Also, the monitoring device may be designed to detect the sound produced by termites as they feed on the monitoring device.

(c) Detection of presence of termites. Upon the detection of the presence of termites in the monitoring device, the monitoring device is removed from the station housing (or soil) and replaced with a toxicant-containing matrix, in a toxicant delivery device (bait tube). Termites that are captured in the monitoring device can be extracted and gently tapped into an upper chamber of the toxicant delivery device. This upper chamber is the recruiters' chamber. In order to exit, the termites must then move through the toxicant-containing matrix to reach the exit points. No toxicant needs to be used unless termites are detected from the monitoring procedure (or are otherwise known to be present), thereby eliminating the use of any unnecessary toxicant. When termites are detected, the toxicant-containing matrix is utilized until no termite activity is detected in the toxicant delivery device. At that time, monitoring devices can be used again. In addition to the practice of replacing monitoring devices with toxicant delivery devices, another embodiment of the invention comprises a monitoring device which remains in place and a toxicant delivery device which can be added to, or fitted around, the monitoring device if the need arises to deliver toxicant.

EXAMPLE 2

Preparation of Toxicant-containing Matrix

The toxicant-containing matrix can comprise cellulose, preferably in the form of a powder or small particles, and the active ingredient of a toxicant. Cellulose in the form of powder allows for a more homogeneous mixture of cellulose and toxicant and facilitates packing and handling. A humectant component can be added to the matrix to maintain moisture content. In one embodiment of the invention, a Methocel® solution of about 1% to about 5% can be used effectively. Methocel® is particularly advantageous because it is a non-nutrient humectant that does not allow microbial growth. An about 1-2% solution is preferred. Moisture content can be varied according to the preferences of different termite species. A preferred embodiment of the invention employs a matrix comprising sawdust as the cellulose component, and water sufficient to yield a moisture content of approximately 50% to about 90% by weight. A moisture content of about 60-80% is preferred. Water content can be varied but should be adequate to thoroughly moisten the dry components of the matrix The preferred consistency of the final matrix is that of a semi-solid paste whereby the sawdust or wood flour can be compacted together and formed or shaped. Sawdust containing about 80% water was found to stimulate feeding by the native subterranean termites (*Reticulitermes* species) and the Formosan subterranean termite, *C. formosanus*.

Further studies have shown that sawdust from hardwood species such as, for example, oak, beech, birch, or maple is preferred by some termites. This was a surprising result because it previously was widely assumed that termites preferred soft wood which is easier to eat. Practical considerations may, however, militate in favor of using softer woods in some circumstances. As used herein, reference to "sawdust" means fine wood particles which may be so fine as to be known as wood flour, and which may be produced from wood by any suitable process as well as by sawing wood. Furthermore, the matrix can be made a preferred food by suitable choice of the species of timber and also suitable choice of the maximum particle size. The exact species of termite to be eradicated will indicate the optimum wood flour and the optimum particle size.

A procedure for the preparation of the toxicant-containing matrix used for the toxicant delivery step is conducted as follows:

1. Hardwood sawdust or wood flour is mixed with water in proportions of approximately 80% water (w/w). Alternatively, the water component can be a 1-2% Methocel® solution.
2. Toxicant is thoroughly mixed into the sawdust/water matrix to result in a homogeneous final concentration. When using hexaflumuron, this concentration may be approximately 5000 ppm.
3. The toxicant-containing matrix can be adjusted with additional water or sawdust to achieve a semi-solid formable consistency which can be packed into the station housing or, preferably, into a casing to form a bait tube.
4. The toxicant-containing matrix can be stored in a moisture-tight and air-tight packaging to maintain the appropriate moisture content.

EXAMPLE 3

Construction of Station housing

In one embodiment of the invention, the station housing can comprise a rigid tube which is pointed at one end and closeably open at its opposite end. The tube is preferably made of a non-biodegradable, durable material which is not attractive to, nor eaten by, termites. The station housing should be made of a material which resists decay or corrosion when exposed to moisture, especially when buried underground for a period of time. The texture of the station housing may be coarse. The station housing will typically comprise entry points which enable termites to have access to the monitoring device or toxicant-containing matrix within. These entry points should not be so large or numerous as to compromise the durability or structural integrity of the station housing or allow dirt or debris to readily enter the inner chamber of the station housing. However, the entry points should be sufficient to provide ready access for termites to the materials within. In one embodiment, numerous entry points on the side of the station housing can lead to inner tubes that may be bent to attach to the inner wall of the toxicant delivery tube. In this embodiment, termites entering the station housing from the soil are directed sideways and into the toxicant The bent inner tubes provide entry points for termites in the soil. Because they are bent sideways, the toxicant-containing matrix cannot be directly accessed from outside. In one embodiment, the entry points have a diameter which is larger than the head of the termite but smaller than the width of its head and two antennae. These holes can have, for example, an inner diameter of about 0.25 cm.

A toxicant-delivery device (bait tube) can be added to the station housing to a level lower than the closeably open end. This level may be, for example, about 2.0 cm below the end. A plastic insert forming a chamber can be placed into the bait tube. This insert can form a recruiter chamber. The chamber can have holes in the end which contact the bait tube so as to allow termites to exit the chamber by entering the bait tube. The chamber may also have very small holes to facilitate air flow. There may be, for example, six holes having an inner diameter of about 0.25 cm. Vertical tubings extending from the holes of the insert can be punctured into the toxicant-containing matrix. This arrangement also helps to tamper-proof the station housing because the toxicant-containing matrix cannot be accessed from any external opening of the bait station. The plastic insert can have a detachable cap at the end of the chamber opposite the bait tube. The detachable cap is either engaged with a snap-on attachment or can be threadedly engaged. Preferably, the cap is made child-proof. The closed chamber thus provides a location to place termites to be used for self-recruitment.

EXAMPLE 4

Horizontal Station housings for Population Suppression of Subterranean Termites

Placement of vertical type station housings is difficult in some locations with rocky soil. Moreover, some termite species tend to forage near the soil surface, making it unnecessary to place a station as deep as that of the vertical type.

Therefore, one embodiment of the subject invention involves the use a horizontal station housing that can be placed near soil surface.

Figure 6A:
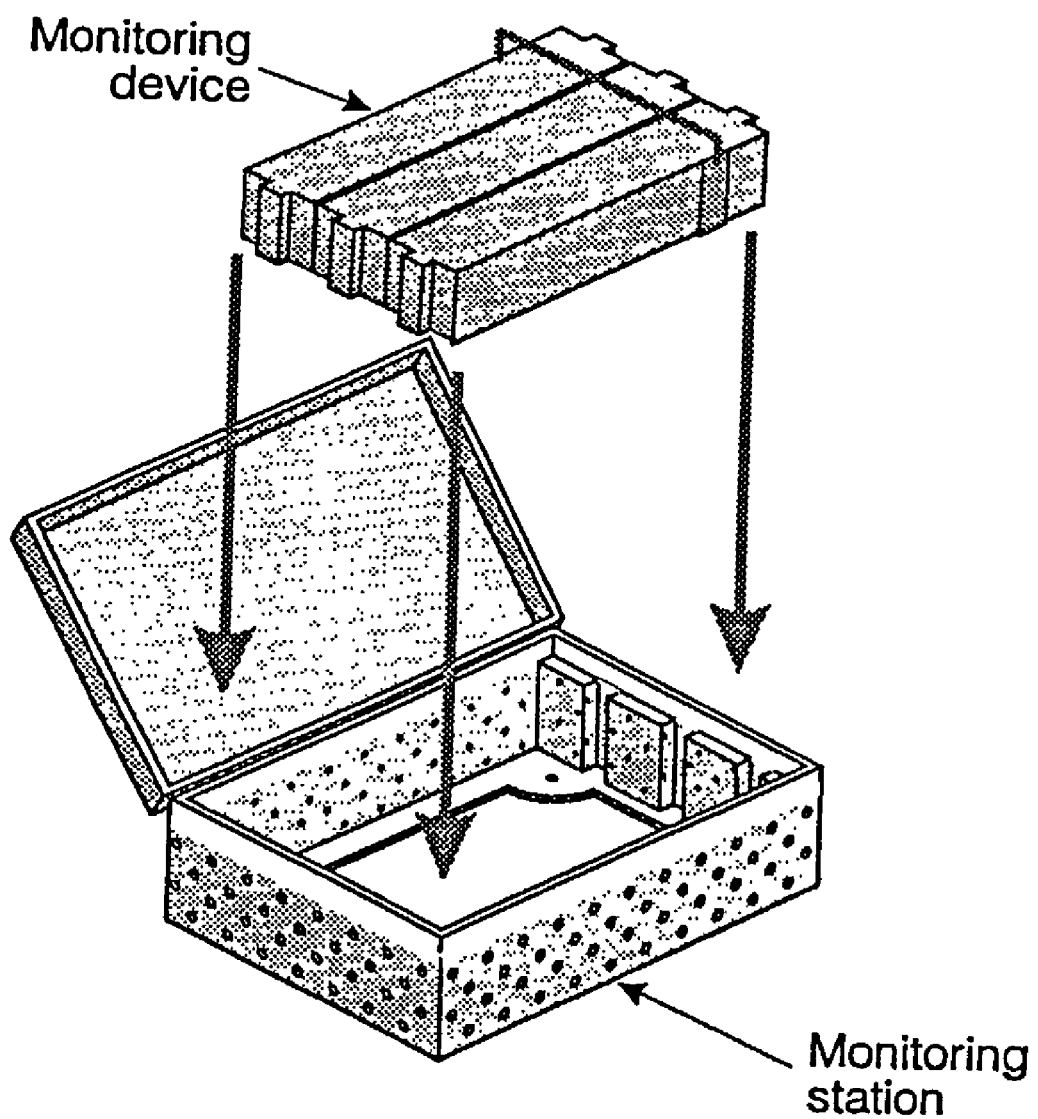
FIG. 6 shows one example of a horizontal monitoring device and station.
Figure 6B:
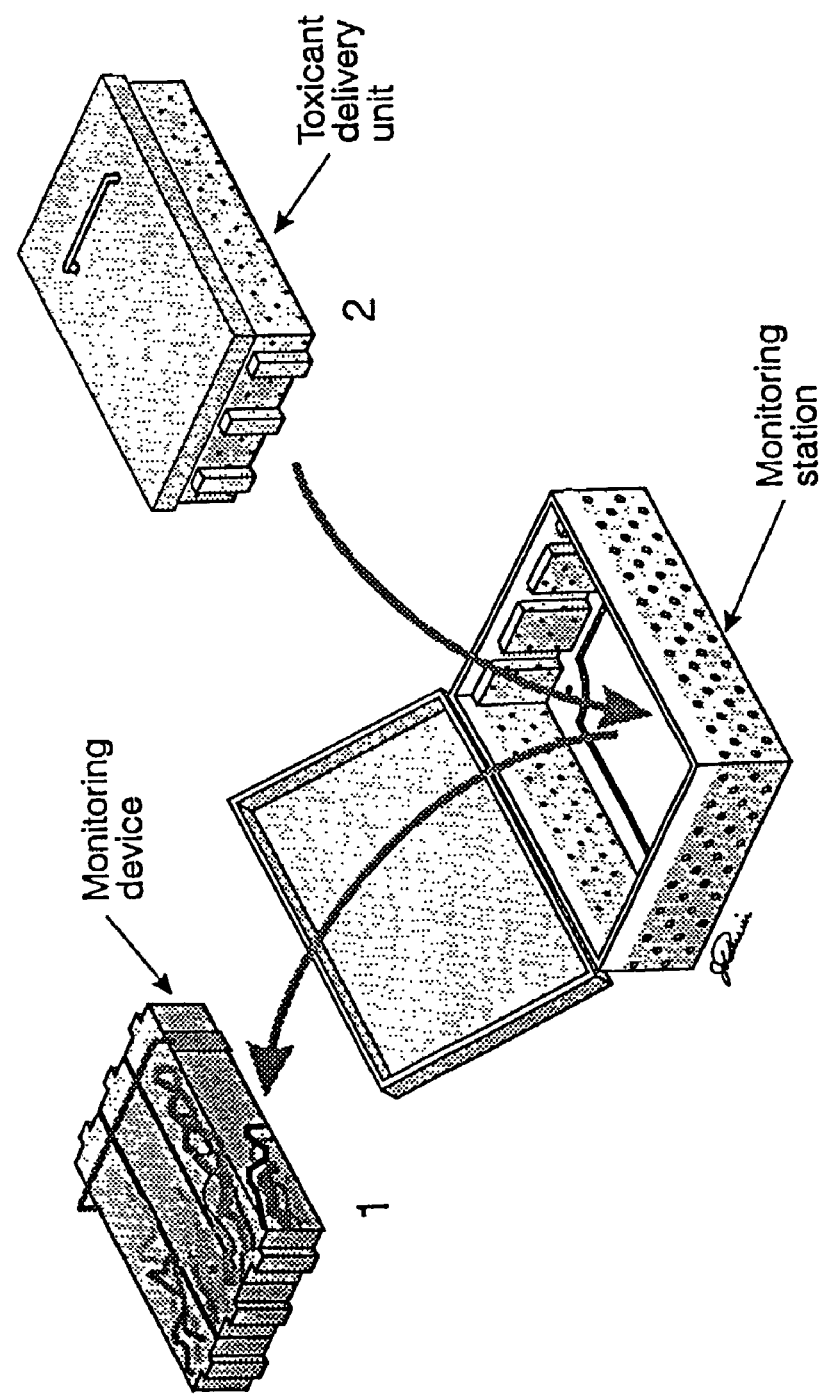
Figure 7A:
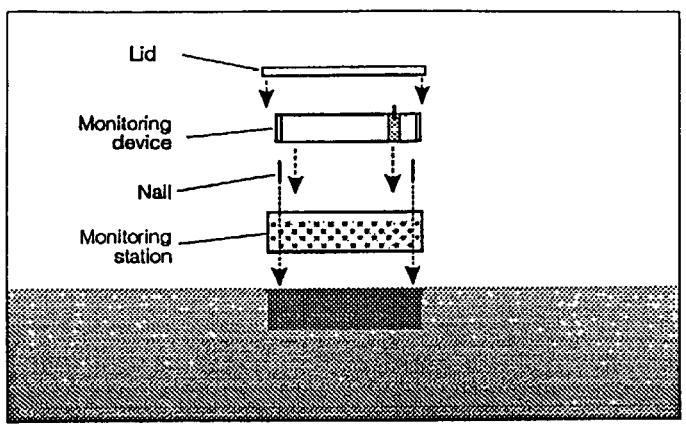
FIGS. 7a-7d show one example of the use of a horizontal monitoring device and toxicant delivery system.
Figure 7B:
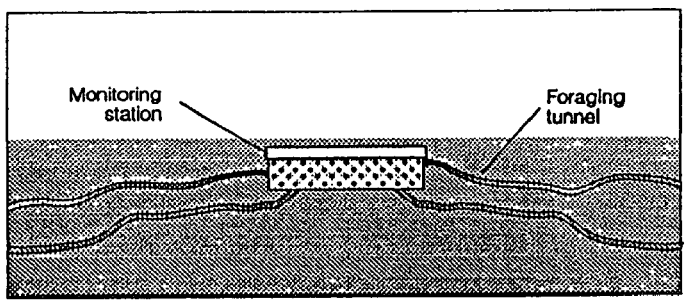
Figure 7C:
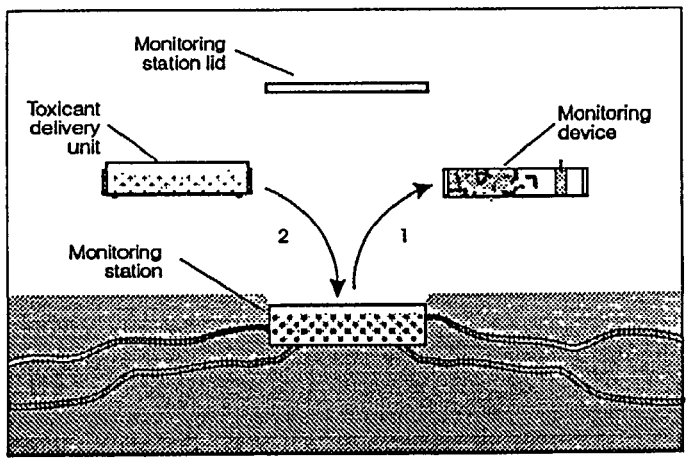
Figure 7D:
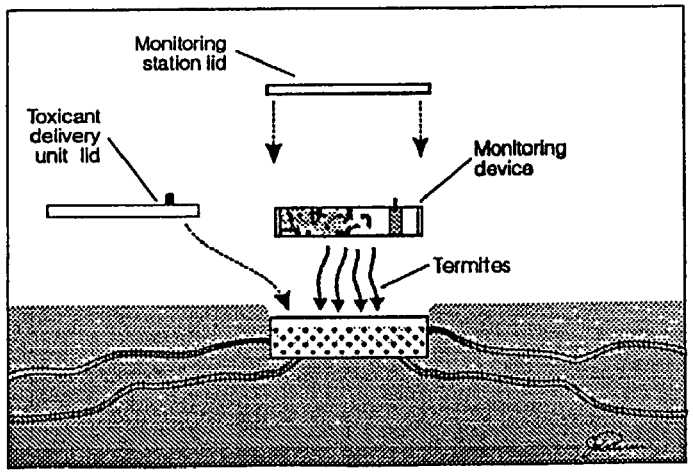

Station housing. The station housing can be comprised of a container with a cut-out bottom. As an example, this container may be about 21.5×16×5.5 cm. Numerous holes can be drilled through the four vertical walls of the container. These holes can be, for example, about 3 mm in diameter inside and about 0.6 mm in diameter outside. This hole arrangement prevents soil invasion into the housing. Inner and outer walls can be sanded to provide a surface suitable for termites to walk on. A monitoring device can be made, for example, of three wooden pieces bound together with a support strip attached to a handle. The monitoring device can be placed inside the container and can be removed using an attached handle with minimum disturbance to termites (FIG. 6).

Toxicant delivery. A container that fits within the station housing can be used as a toxicant delivery device. This container may be, for example, about 19.3×13.5×4.5 cm. Except for a removable cover, numerous holes through all sides of the container can be provided for termite entry. These holes may be, for example about 0.24 cm in diameter. Holes can extend inside the toxicant delivery device with inner tubes bent at about 90° to prevent tampering with the toxicant-containing matrix. The inner and outer walls of the toxicant delivery device can be sanded. The toxicant delivery device can be filled with the toxicant-containing matrix up to, for example, about 1 cm from the top of the container and covered with a lid.

Operating procedure. A station housing containing wooden pieces as the monitoring device is placed beneath the ground and covered with a thin layer of soil (FIGS. 9a, 9b). This thin layer of soil can be, for example, about 1 cm. Monitoring devices are then checked periodically for termite activity. Monitoring devices infested with termites are gently lifted and replaced by the toxicant delivery device containing the toxicant-containing matrix (FIG. 7). Termites extracted from the boards are gently tapped into the upper 1 cm deep chamber of the toxicant delivery device (FIG. 9d), leaving the colony recognition semiochemicals in the toxicant-containing matrix to "self-recruit" nestmates into the toxicant delivery device.

EXAMPLE 5

The procedures, materials, and apparatuses of the subject invention can be readily adapted for use for the control of termites attacking croplands, forests, golf courses, and other non-structural targets. The same general materials and methods may be utilized with minor modifications, readily apparent to those skilled in the art, to achieve optimal results.

EXAMPLE 6

Above-ground Monitoring and Toxicant Delivery

In urban areas where the soil which surrounds a structure is often paved with cement, or asphalt, or some like material the placement of the monitoring and/or toxicant delivery devices in or on the ground may not be practical. Termite infestation, however, is no less of a problem in these urban areas. Therefore, an alternative application and design of the described invention comprises a monitoring and/or toxicant delivery station which can be used in an above-ground system. Such a system is also of value anytime that an above-ground infestation is observed.

An above-ground design is illustrated in FIG. 5. This above-ground system can comprise a station housing which is placed or mounted in or on the wall of a structure. The station housing can comprise a frame which is designed to simultaneously fit snugly against the wall and a wooden door frame, a molding, or the like. In one embodiment, the station housing can enclose a toxicant-containing matrix, substantially as described above, wherein the toxicant-containing matrix can be packaged in various shapes and sizes, for example, a rectangular box shape, to facilitate their use with the above-ground system housing. The above-ground station housing can be substantially open at the side which faces or is mounted against the wall. The side of the station housing facing outward is closeably open, wherein a hinged lid or a separate lid can be placed over the opening. The lid serves to prevent exposure to toxicants by persons encountering the station housing. The lid can further comprise a locking means to prevent inadvertent exposure by children or others. The cover can also serve to prevent moisture loss from the toxicant-containing matrix. Moisture loss can also be prevented by the packaging of the toxicant, wherein it is preferable to package the toxicant-containing matrix in a casing which is edible by termites. Such casings can be cardboard, paperboard, paper, and the like as described above. A preferable material for packaging the toxicant-containing matrix is wax-paper due to its moisture-retaining characteristics.

After a station housing is attached to a wall, fence, tree stump, tree trunk, or other structural member, contact with the termite galleries can be facilitated by drilling a hole through the structural member into the gallery area. Initially, a cellulose monitoring device may be placed in the housing. If termites are detected, the monitoring device can be replaced with a toxicant-containing matrix and collected termites used for recruitment. In case of known termite activity, a toxicant-delivery device may be placed in the station housing without the placement of a monitoring device.

In one embodiment, cement or asphalt can effectively act as a station housing. For example, a hole may be drilled into cement, either inside or outside a structure, to gain access to the soil below. The monitoring device may then be placed into the drilled hole such that the device makes contact with soil. The device may then be monitored and replaced with a toxicant-containing matrix, preferably within a casing, if termite activity is observed. Of course, a station housing may also be used in this instance by inserting the station housing into the hole drilled in the cement. When the cement hole is used as the station housing, a rubber stopper or equivalent device can serve as the top, or cover/lid.

Above-ground monitoring and toxicant delivery schemes can also be widely adapted for use in trees.

EXAMPLE 7

Dyes may be incorporated into the matrix to assist the applicator in identifying termite colonies and foraging range of termites feeding on a monitoring article or toxicant bait. Appropriate dyes include, but are not limited to, Nile Blue A and Sudan Red 7B. A laboratory study showed that termites accepted bait matrix containing 0.01-0.05% Nile Blue A, and were visibly stained after feeding on the dyed material.

EXAMPLE 8

Field Testing Using Matrix Containing Hexaflumuron

1. Procedures. Field colonies of the Formosan subterranean termite, *C. formosanus*, and the eastern subterranean termite, *R. flavipes*, were selected for testing. Termite activity was measured 1-2 years before the introduction of a hexaflumuron treated matrix. Monitoring stations contained pre-weighed wood blocks surrounded by plastic containers buried beneath the soil surface. Wood weight loss of a block was determined monthly or bimonthly to represent activity of the subterranean termite colony being tested. A multiple mark-recapture program was conducted to estimate the foraging population size and foraging territory of each tested colony. A mark-recapture program refers to a procedure wherein a known number of termites are marked using a dye marker such as Nile Blue A and then released back to the colony. A week later, termites are recaptured from the same colony and the ratio of marked and unmarked termites are recorded. Assuming the initially marked termites are distributed homogeneously among colony population, the total population is calculated using the number of initially marked termites and the ratio of marked and unmarked termites (Begon, M. [1979] *Investigating animal abundance: capture-recapture for biologists*, University Park Press, Baltimore, Md.). Termite activity was monitored throughout the toxicant delivery program. When possible, another mark-recapture program was conducted to estimate the post-toxicant delivery population of a colony.

2. Toxicant-containing matrix. Pine or spruce sawdust was impregnated with an acetone solution of hexaflumuron to yield concentrations of 500-5,000 ppm (dry wt AI/dry wt sawdust) upon evaporation of acetone. The toxicant-containing matrix was composed of 20% treated sawdust and 80% of agar or Methocel® solution (2%). A station housing was composed of a plastic tubing (2.9 cm diam. I.D. by 16.5 cm high, one end closed, the other open) filled with approximately 80 g of toxicant-containing matrix. This leaves approximately 5 cm height of open space on the open end of the tubing. Six layers of 9 holes (0.238 mm diameter) were pre-drilled in the side of the tubing.

3. Monitoring. Wooden stakes (3.4 cm by 3.4 cm by 30 cm) were driven 20-25 cm into the ground. Once infested by termites, the wooden stake was gently pulled out of the soil, leaving a hole of ca. 3.4 cm by 3.4 cm and 20-25 cm deep. A station housing was inserted into the hole. Termites were extracted from the infested stakes and placed into the open space (5 cm high by 2.9 cm diameter) on the open end of the toxicant bait station. The extracted termites were forced to tunnel through the toxicant-containing matrix to return to the colony, and to recruit nestmates into the station housing. To compare the efficacy of self-recruiting procedure in enhancing the toxicant intake, this self-recruiting procedure was omitted in some station housings. Station housings were checked monthly. The amount of matrix consumed by termites from each station was subjected to the analysis of variance using a completely randomized design ($P<0.05$) to determine the significant difference in matrix consumption between stations with the self-recruiting procedure and those without.

Results:

Experiment 1. The foraging population of this *R flavipes* colony was estimated at 476,000 in September. Infestations by this colony were found in the door and door-frame of a nearby building. Wood weight loss from the three monitoring devices was approximately 2 g/station/day during the summer. The activity declined during the winter to approximately 0.5 g/station/day. Three bait tubes were introduced in February. By April, no termite activity was found in any of the station housings. A total of 26 g of toxicant-containing matrix was consumed by this termite colony. The amount of active ingredient (AI) consumed was 3.87 mg. Because of the absence of termite activity after April, it was concluded that the entire colony of over 400,000 termites was eliminated by the consumption of 3.87 mg hexaflumuron within two months.

Experiment 2. The foraging population of this *R. flavipes* colony was estimated at 730,000 in September. This colony was located in a non-residential area. Termite infestations were found in trees and fallen logs of pine and oaks. From September through the following spring, wood weight loss from the six monitoring devices was approximately 2 g/station/day. Starting in April, eleven station housings were used to deliver toxicant-containing matrix. In June, termites maintained the activity level of 1.8 g/station/day. By July, however, the activity was reduced to 0 g/station/day. During the three months (April-June) baiting period, a total of 122 g toxicant-containing matrix and 20 mg AI was consumed. No termite activity was recorded in this location after July. We conclude the 730,000 termites were eliminated by consuming 20 mg of hexaflumuron.

Experiment 3. Structural infestation of this *R. flavipes* colony persisted in a two-story building (approximately 1,500 $m^2$) for at least 3 years. Residents reported annual spring swarming from the structure for five consecutive years. Soil termiticide treatments had been done by a pest control firm annually since the erection of the building in 1986. Despite the soil termiticide treatments, the foraging population of this *R. flavipes* was estimated at 2,847,000 in May. Foraging territory was approximately 1,782 $m^2$. Mean wood weight loss from the 13 station housings with monitoring devices ranged 2-4 g/station/day. Following the introduction of toxicant-delivery devices at 27 stations in August, the activity was reduced to 0.1 g/station/day in September. Termites, however, remained active in stations in October and November. By December, no termite activity was detected from any of the stations. During the four month toxicant-delivery period (August-December), a total of 2,997g toxicant-containing matrix and 1,539 mg AI was consumed by this *R. flavipes* colony. Residents of the building reported that this was the first time within the last five years that they did not see the termites swarming. No soil termiticide treatment was done the following year. In March of the following year, termites were collected in one of the monitoring devices. Because no dyed termites were found from this collection, we speculated that a nearby colony might have migrated into the territory of the baited colony. A mark-recapture program conducted in March-April estimated 260,000 foraging termites in this new colony. Assuming this is the remaining of the original colony, the toxicant-delivery program conducted in August-December had eliminated over 2.5 million termites.

Experiment 4. Foraging activity of this *C. formosanus* colony has been monitored in an 11-story high rise. Numerous soil termiticide treatments were done to prevent structural infestation by this *C. formosanus* colony. Foraging population was estimated at 1,047,000 in September. The foraging territory extended to 1,614 $m^2$. Mean wood weight loss was 2-4 g/station/day. Foraging activity typically declined in winter but often peaked during summer months (5-10 g/station/day). Five toxicant/delivery devices were introduced in April. The foraging activity was reduced to less than 2 g/station/day, and remained at the same low level until October. By November, no termites were found in the stations, but slight feeding activity was observed in a few stations until February. During the toxicant-delivery program (April-February), 847 g of toxicant-containing matrix and 233 mg AI were consumed by this *C. formosanus* colony. We concluded the colony of 1.0 million termites was eliminated after consuming 233 mg of hexaflumuron over a 10-month period.

Experiment 5. Despite repeated soil termiticide treatments and a fumigation following the discovery of structural infestations by this *C. formosanus* colony in a high rise, foraging activity remained strong (mean wood weight loss: 6-10 g/station/day). Activity of this colony did not decline even in winter months. Foraging population was estimated at 2,431,000 in March. Over 90% of the toxicant-containing matrix of stations introduced in May was consumed within a month. Foraging activity in May-July was slightly reduced (5 g/station/day). Subsequently, the mean wood weight loss was further reduced to near zero in July-October. After November, no termite activity has been recorded in any of the stations. During the 6-month toxicant-delivery period (May-November), a total of 89 station housings with toxicant-delivery devices were used. We concluded that the colony of 2.4 million termites was eliminated by the consumption of 742 mg hexaflumuron.

Experiment 6. Infestations by this *C. formosanus* colony were found in the utility room of a high rise. Foraging activity was detected along the front yard of this building. The foraging territory extended up to 185 m from one end to the other. This *C. formosanus* colony consumed wood at a rate of approximately 5-10 g/station/day from 10 stations. The foraging population was estimated at 1,225,000 in April. Following the introduction of toxicant-delivery devices in July, foraging activities steadily declined to near zero in October. After October, slight termite activity (<1 g/station/day) remained in one station. Using termites collected from this station, we conducted a mark-recapture program in March and estimated 104,000 termites in the remaining colony. A total of 42 stations were used during the 5-month toxicant-delivery period (July-December), from which 1,182 g of toxicant-containing matrix and 259 g AI were consumed. We concluded the 259 mg of hexaflumuron reduced the population size of this colony from 1.2 million termites in April to 104,000 the following March.

EXAMPLE 9

Effects of the Self-recruiting Procedure on Toxicant Bait Consumption

Significantly more ($P<0.05$) toxicant-containing matrix was consumed from station housings that received termites collected from the monitoring devices (referred to as "self-recruited" bait stations) than stations that were simply placed in the holes from which infested devices were pulled ("not self-recruited" bait stations). In one experiment, the mean weight of toxicant-containing matrix consumed by *C. formosanus* from self-recruited stations was 35.8 g/station while those of not self-recruited stations was 6.5 g/station. With *R. flavipes*, the mean weight of consumed toxicant-containing matrix was 39.2 and 17.2 g/station for self-recruited stations and not self-recruited stations, respectively.

When more than 1% of the toxicant-containing matrix was consumed from a station housing, the station was considered attacked by termites. Using this criteria, 83% of self-recruited stations were attached by *C. formosanus*, while only 59.3% of not self-recruited stations were attacked. With *R. flavipes*, the attack rate for self-recruited stations was 94.7%, while 75% of the not self-recruited stations were attacked.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A delivery system for controlling termites wherein said delivery system comprises a toxicant-free monitoring device, a toxicant delivery device comprising a toxicant-containing matrix, and a durable non-termite-edible delivery housing that simultaneously holds the toxicant-free monitoring device and the toxicant-containing matrix, wherein the delivery housing has a plurality of openings permitting termite access to the toxicant-free monitoring device and the toxicant-containing matrix, the matrix of the toxicant-containing matrix comprises a cellulose-containing material, wherein the toxicant-containing matrix is present after termites are detected; said delivery system providing a delayed lethal effect on termites thereby permitting the termites to return to an associated nest after coming in contact with said toxicant containing matrix.

2. The delivery stem of claim 1 wherein the delivery housing is made of plastic, aluminum, or stainless steel.

3. The delivery system of claim 1 wherein the toxicant-containing matrix is enclosed in a casing permitting termite access to the toxicant-containing matrix.

4. The delivery system of claim 3 wherein the casing is made of a polymeric material having openings through which termites can pass.

5. The delivery system of claim 1 wherein the monitoring device comprises a cellulose-containing material.

6. The delivery system of claim 1 further comprising a cover for the delivery housing.

7. The delivery system of claim 1 wherein the toxicant of the toxicant-containing matrix is a slow acting termiticide.

8. The delivery system of claim 7 wherein the slow-acting termiticide is an acyl urea.

9. A method for controlling termites wherein said method comprises positioning a durable non-termite edible delivery housing at a location accessible to termites, placing a toxicant-free monitoring device and a toxicant delivery device comprising a toxicant-containing matrix within said delivery housing so that both said toxicant-free monitoring device and toxicant-containing matrix are held simultaneously by said delivery housing, wherein the delivery housing has a plurality of openings permitting termite access to the toxicant-free monitoring device and toxicant-containing matrix, and wherein the toxicant-containing matrix is present after termites are detected; said delivery system providing a delayed lethal effect on termites thereby permitting the termites to return to an associated nest after coming in contact with said toxicant containing matrix.

10. The method of claim 9 wherein the delivery housing is made of plastic, aluminum, or stainless steel.

11. The method of claim 9 wherein the toxicant-containing matrix is enclosed in a casing permitting termite access to the toxicant-containing matrix.

12. A method of claim 11 wherein the casing is made of polymeric material having openings through which termites can pass.

13. The method of claim 9 wherein the toxicant of the toxicant-containing matrix is a slow-acting acyl urea.

14. The method of claim 9 wherein said delivery housing further comprises a cover.

15. The method of claim 9 wherein the delivery housing is positioned in a cavity in the ground.

16. The method of claim 9 wherein the monitoring device is placed before said delivery housing is positioned.

17. The method of claim 9 wherein the monitoring device is placed after said delivery housing is positioned.

\* \* \* \* \*